United States Patent [19]
Vanek et al.

[11] Patent Number: 5,983,426
[45] Date of Patent: Nov. 16, 1999

[54] VERSATILE PATIENT RESTRAINT SYSTEM

[75] Inventors: Denis W. Vanek, Cleveland; Dean A. Putzbach, Mentor, both of Ohio

[73] Assignee: Picker International, Inc., Highland Heights, Ohio

[21] Appl. No.: 09/066,092

[22] Filed: Apr. 23, 1998

[51] Int. Cl.⁶ .................................................. A61G 13/10
[52] U.S. Cl. ...................... 5/621; 5/601; 5/623; 5/503.1
[58] Field of Search ................... 5/621, 601, 622, 5/623, 624, 628, 494, 503.1; 378/209; 128/870

[56] References Cited

U.S. PATENT DOCUMENTS

| | | | |
|---|---|---|---|
| 3,700,229 | 10/1972 | Kurokawa et al. | 2/621 |
| 4,484,571 | 11/1984 | Velasquez | 5/621 |
| 4,779,858 | 10/1988 | Saussereau | 5/601 |

*Primary Examiner*—Alexander Grosz
*Attorney, Agent, or Firm*—Fay, Sharpe, Beall, Fagan, Minnich & McKee

[57] ABSTRACT

A versatile patient support and restraint system is provided. It includes a couch (14) having a top surface (22) for supporting a patient being examined within an examination region (12). Two substantially parallel grooves (20) are formed along a longitudinal direction in the top surface (22) of the couch (14) on opposite sides thereof. Two removable tracks (30) extending in a longitudinal direction are removably seated in the grooves (20). Adjustable restraint straps for securing the patient to the couch (14) are also provided. The adjustable restraint straps include pins attached to opposing ends of the adjustable restraint straps. The pins selectively engage the two removable tracks (30) thereby selectively securing opposing ends of the adjustable restraint straps to opposite sides of the top surface (22) of the couch (14).

20 Claims, 7 Drawing Sheets

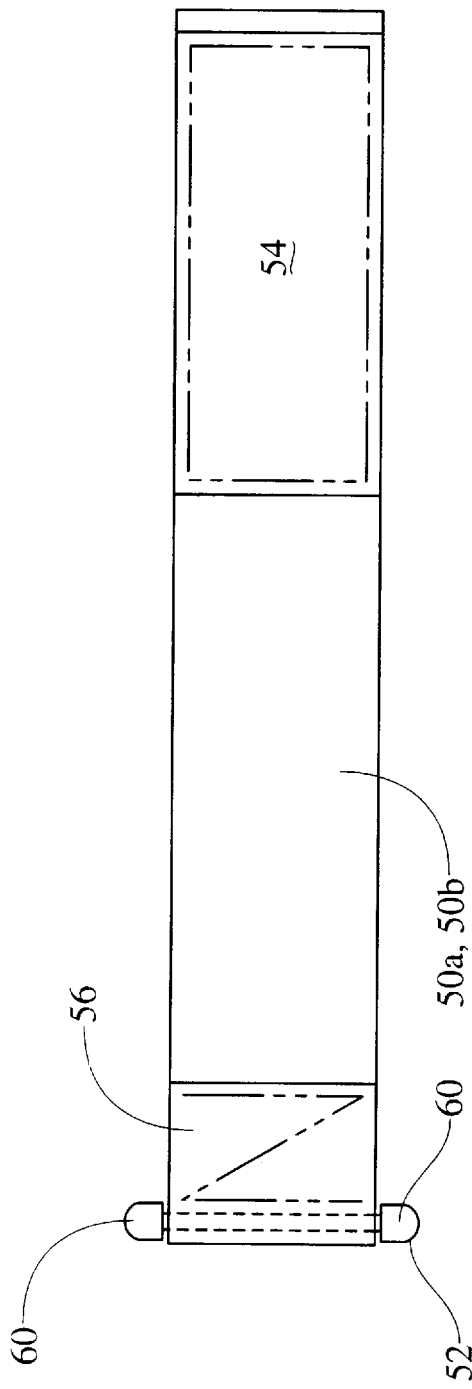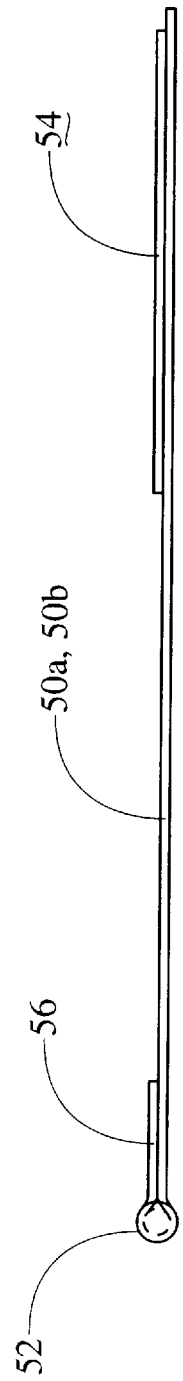
Fig. 3B
Fig. 3C

VERSATILE PATIENT RESTRAINT SYSTEM

BACKGROUND OF THE INVENTION

The present invention relates to the art of patient restraints. It finds particular application in conjunction with patient restrains for couches and/or tables employed in diagnostic imaging apparatus (i.e. magnetic resonance (MR) systems, computer tomography (CT) scanners, gamma cameras, and the like), and will be described with particular reference thereto. However, it is to be appreciated that the present invention is also amenable to other applications wherein the immobilization and/or securing of patients is desired.

In diagnostic imaging, typically patients or subjects being examined or whose anatomy is being imaged are supported or suspended in an examination region by a patient table or couch. In order to reduce or eliminate motion artifacts in the resulting image, it is advantageous to immobilize the patient and/or secure him to the couch. Additionally, during imaging, it is often desirable to have certain patient support equipment or accessories remain with the patient. For example, the patient may have an IV inserted in an arm such that it is desirable to have the arm off to the side of the patient table or couch and have an IV bag elevated above the patient. Moreover, in diagnostic image-guided interventional procedures, it may be desirable to have a shelf or sideboard accompanying the patient table or couch which would hold the attending physicians or surgical team's medical instruments, surgical tools, and the like.

Previous systems and techniques have addressed these issues. However, these systems and/or techniques were accompanied by certain inherent drawbacks. Some systems and/or techniques lacked the versatility desired. Other systems and/or techniques employing grooves in the top surface of the couch lack the desired ease of sanitation. That is to say, the grooves which often collected dirt and other outside contaminants were difficult to clean and/or otherwise maintain. Still other systems were too complicated and/or lacked a continuous range of adjustability. A continuous and large range of adjustability provides for improved immobilization of various size patients and/or varying anatomies. This, in turn, results in a greater reduction of motion artifacts and ultimately leads to improved image quality.

The present invention contemplates a new and improved patient restraint system which overcomes the above-referenced problems and others.

SUMMARY OF THE INVENTION

In accordance with one aspect of the present invention, a versatile patient support and restraint system is provided. It includes a couch having a top surface for supporting a patient being examined within an examination region. Two substantially parallel grooves are formed along a longitudinal direction in the top surface of the couch on opposite sides thereof. Two removable tracks extending in a longitudinal direction are removably seated in the grooves. Also provided are adjustable restraint straps for securing the patient to the couch. The adjustable restraint straps include pins attached to opposing ends of the adjustable restraint straps. The pins selectively engage the two removable tracks thereby selectively securing opposing ends of the adjustable restraint straps to opposite sides of the top surface of the couch.

In accordance with a more limited aspect of the present invention, the two removable tracks include hollow longitudinally extending cylindrically shaped portions with external diameters sized to fit in the two grooves and internal diameters sized to receive the pins of the adjustable restraint straps. Longitudinally extending gaps are formed in the cylindrically shaped portions creating openings along tops thereof. The gaps are sized to permit the adjustable restraint straps to pass therethrough while prohibiting the pins from passing therethrough.

In accordance with a more limited aspect of the present invention, the gaps further include along lengths thereof insertion regions having lengths substantially equal to lengths of the pins. At the insertion regions, the gaps are enlarged to permit the pins to pass therethrough.

In accordance with a more limited aspect of the present invention, the two removable tracks include pairs of track tabs running longitudinally along and extending radially from the cylindrically shaped portions. The pairs of track tabs define the gaps therebetween. Pairs of tapered flaps extend from the pairs of track tabs such that when the two removable tracks are seated in the two grooves, the pairs of tapered flaps are urged toward the top surface of the couch substantially sealing off the two grooves from outside contaminants.

In accordance with a more limited aspect of the present invention, the pins are selectively positioned within the cylindrically shaped portions of the removable tracks along continuous longitudinal ranges thereof.

In accordance with a more limited aspect of the present invention, the adjustable restraint straps are adjustable in length and include two parts. The two parts have securing ends where the pins are attached and opposing joining ends where a fastener is attached that selectively joins the two parts together.

In accordance with a more limited aspect of the present invention, a sideboard is included. The sideboard has an engagement member having a plurality of slots. The engagement member selectively engages one of the two removable tracks thereby selectively securing it to the top surface of the couch. A support member has a surface with a plurality of support member tabs along one side thereof. The plurality of the support member tabs are selectively engaged with the plurality of slots of the engagement member to selectively secure the support member to the engagement member.

In accordance with a more limited aspect of the present invention, the engagement member includes a longitudinally extending cylindrical shaft for selective engagement with one of the two removable tracks. A shaft tab radially extends from the shaft and has the plurality of slots formed therein.

In accordance with a more limited aspect of the present invention, the shaft is sized to fit in the cylindrically shaped portions of the removable tracks without passing through the gaps.

In accordance with a more limited aspect of the present invention, when engaged with one of the two removable tracks, the shaft is selectively positioned along a continuous longitudinal range of one of the two removable tracks such that the shaft tab passes through the gap.

In accordance with a more limited aspect of the present invention, the plurality of support member tabs are inclined at a predetermined angle with respect to the surface of the support member.

In accordance with a more limited aspect of the present invention, the support member includes a bar attached to an underside of the surface of the support member such that when the support member is engaged with the engagement member, the bar abuts up against the shaft tab.

In accordance with a more limited aspect of the present invention, the support member includes a lip along a side of the support member opposite the plurality of support member tabs which lip is inclined at a predetermined angle with respect to the surface of the support member.

In accordance with a more limited aspect of the present invention, an IV hook for hanging IV bags elevated above the patient is provided. The IV hook has an engagement portion which is selectively engaged with one of the two removable tracks thereby selectively securing the IV hook to the couch. An upwardly extending portion rises from the engagement portion and a hooked portion is included at an end of the upwardly extending portion opposite the engagement portion.

In accordance with another aspect of the present invention, a patient restraint system is provided in a diagnostic imaging apparatus. The diagnostic imaging apparatus includes an imaging device which generates human viewable images of a patient's anatomy, an examination region where the patient is positioned for imaging, and a couch for supporting the patient in the examination region. The patient restraint system includes longitudinal grooves formed in a top surface of the couch. Removable inserts secured in the longitudinal grooves substantially seal off the longitudinal grooves from outside contaminants. Straps for securing the patient to the couch are included. The straps have enlarged ends that are selectively engaged with the removable inserts thereby selectively securing the straps to the couch.

In accordance with a more limited aspect of the present invention, the removable inserts include longitudinally extending hollow portions with external dimensions sized to fit the grooves and internal dimensions sized to receive the enlarged ends of the straps. Longitudinally extending gaps are formed in the hollow portions creating openings along tops thereof. The gaps are sized to permit the straps to pass therethrough while prohibiting the enlarged ends from passing therethrough. Pairs of walls running longitudinally along and extending from the hollow portions define the gaps therebetween. Pairs of flaps extend from the pairs of walls such that when the removable inserts are secured in the grooves, the pairs of flaps are urged toward the top surface of the couch.

In accordance with a more limited aspect of the present invention, the enlarged ends are selectively positioned within the hollow portions of the removable inserts along continuous longitudinal ranges thereof.

In accordance with a more limited aspect of the present invention, a sideboard is included. The sideboard has an engagement member having a plurality of slots. The engagement member selectively engages the removable inserts thereby selectively securing it to the couch. A support member having a surface with a plurality of tabs along one side thereof is included. The plurality of tabs selectively engage with the plurality of slots to selectively secure the support member to the engagement member.

In accordance with a more limited aspect of the present invention, the engagement member includes an enlarged shaft for selective engagement with the removable inserts. The enlarged shaft has dimensions sized to fit the hollow portions of the removable inserts without passing through the gaps. An extending portion having the plurality of slots formed therein extends from the enlarged shaft through the gaps of the removable inserts.

In accordance with a more limited aspect of the present invention, an IV hook for hanging IV bags elevated above the patient is included. The IV hook has an enlarged engagement portion which is selectively engaged with the removable inserts thereby selectively securing the IV hook to the couch. The enlarged engagement portion has dimensions sized to fit the hollow portions of the removable inserts without passing through the gaps. An upwardly extending portion rises from the enlarged engagement portion through the gaps and a hooked portion is included at an end of the upwardly extending portion opposite the enlarged engagement portion.

One advantage of the present invention is that it provides a versatile, high quality patient restraint and support system with relatively simplified construction.

Another advantage of the present invention is the ease with which cleaning and maintenance is performed thereon.

Another advantage of the present invention is the ability to adjust over a continuous range the positioning of patient restraints and support equipment.

Another advantage of the present invention is the unification of the engagement system for the various patient restraints and support equipment to the couch.

Another advantage of the present invention is the ability to employ various widths of patient restraint straps.

Another advantage of the present invention is that improved adjustability of the patient restraints allows for better immobilization of the patient which in turn improves image quality by reducing motion artifacts in diagnostic imaging applications.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIGS. 3B and 3C are bottom and side views respectively of one part of the adjustable patient restraint strap in accordance with aspects of the present invention;

DETAILED DESCRIPTION OF THE PREFERRED EMBODIMENTS

Figures 1A, 1B:
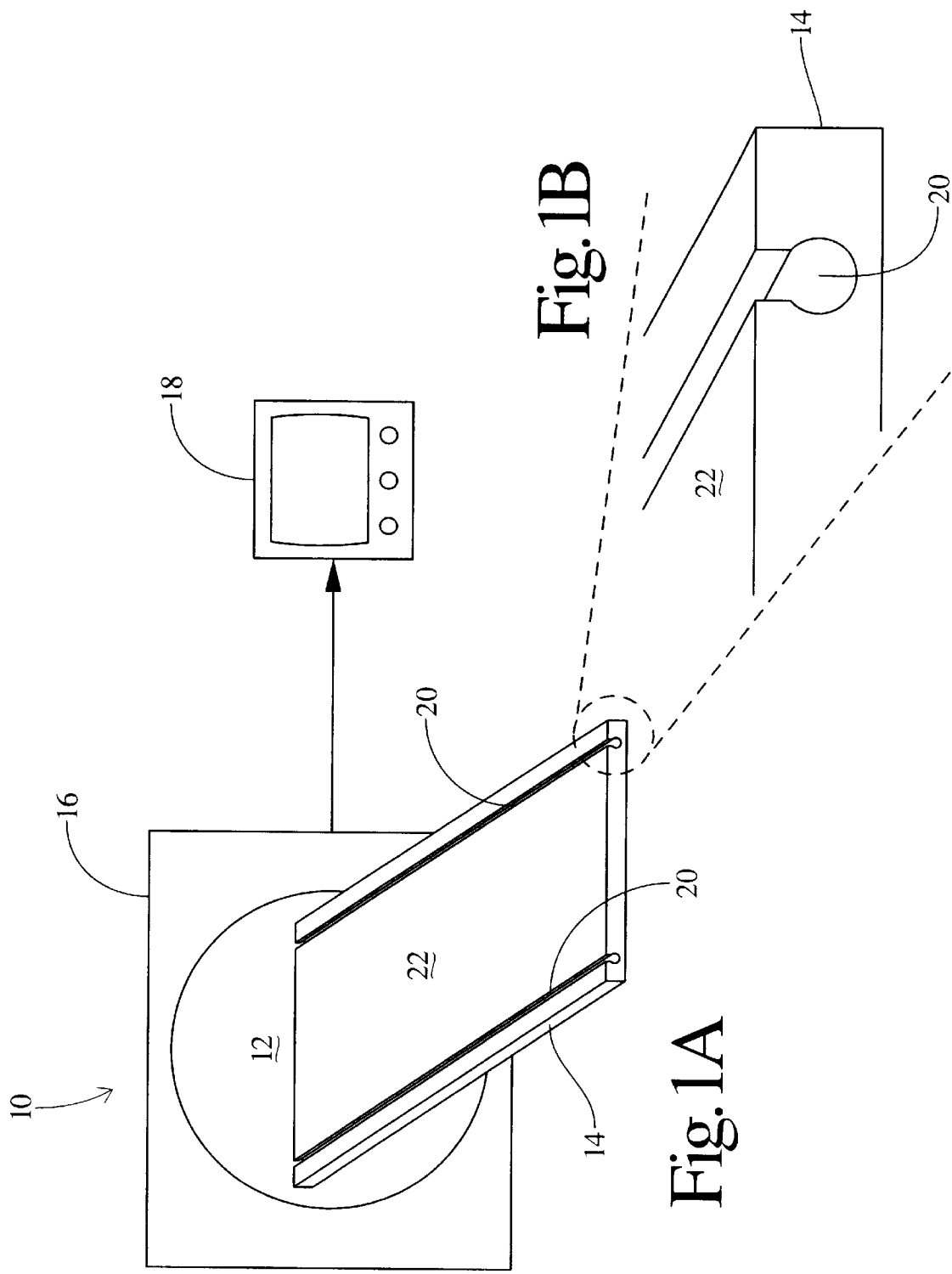
FIG. 1A is a diagrammatic illustration of a diagnostic imaging apparatus having a patient couch with grooves in accordance with aspects the present invention.
FIG. 1B is a blow-up of a portion of FIG. 1A showing the detail of the grooves in accordance with aspects of the present invention.

With reference to FIG. 1A, a diagnostic imaging apparatus 10, such as an MR system, CT scanner, gamma camera, or the like, defines an examination region 12 wherein a patient being examined is positioned for imaging of the patient's anatomy. A patient table or couch 14 supports and/or suspends the patient within the examination region 12. Optionally, the couch 14 is movable so as to be selective insert into and retracted from the examination region 12. Works 16 as are appropriate to the diagnostic imaging apparatus 10 perform manipulations, imaging sequences, and other operations to generate images of the patient's anatomy as desired. The generated images are displayed by a human viewable display such as a video monitor 18.

With reference to FIG. 1B and continuing reference to FIG. 1A, the couch 14 has grooves 20 formed in a top surface 22 thereof. In a preferred embodiment, there are two grooves 20 that run substantially parallel to one another along a length of the couch 14 in a longitudinal direction on opposite sides of the top surface 22 of the couch 14. The grooves 20 are formed to receive removable inserts or tracks 30 illustrated in FIGS. 2A through 2C.

Figure 2A:
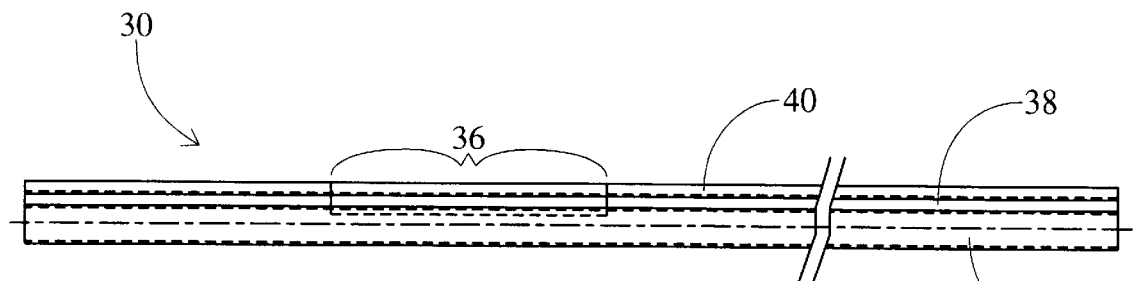
FIGS. 2A through 2C are side, top, and end views respectively of removable tracks or inserts in accordance with aspects of the present invention.
Figure 2B:
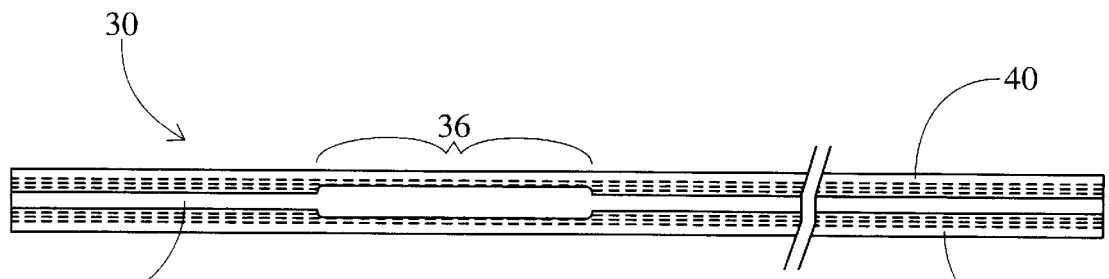
Figure 2C:
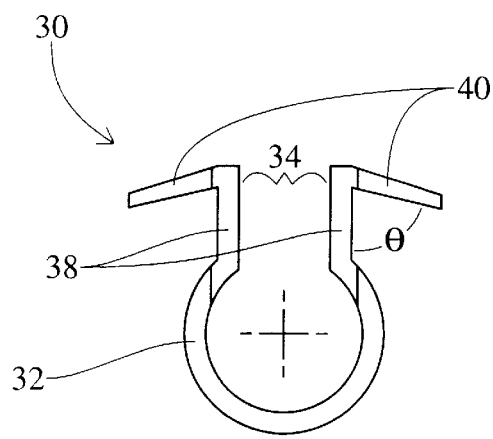

With reference to FIGS. 2A through 2C, the removable inserts or tracks 30 extend in a longitudinal direction and are removably seated or secured in the grooves 20. Preferably, the tracks 30 run the length of the grooves 20 and are formed from a semi-rigid PVC plastic or other suitable material. They are easily installed and removed by inserting them into an end of the grooves 20 at a head and/or foot of the couch 14. The tracks 30 include hollow longitudinally extending cylindrically shaped portions 32 with external diameters sized to fit in the grooves 20. The internal diameters are sized to receive certain parts described later herein. Longitudinally extending gaps 34 are formed in the cylindrically shaped portions 32 creating openings along tops thereof. The gaps 34 are sized smaller than the inner diameter of the cylindrically shaped portions 32 to permit the passing therethrough of certain other parts describe later herein while prohibiting the passing therethrough of parts sized to be received in the inner diameter of the hollow cylindrically shaped portions 32. The gaps 34 include along lengths thereof insertion regions 36 where the gaps 34 are enlarged thereby permitting the passing through of parts sized to be received in the hollow cylindrically shaped portions 32 which parts otherwise would be too large to pass through the gaps 34.

The tracks 30 have pairs of track tabs or walls 38 running longitudinally along and extending radially from the cylindrically shaped portions 32. The pairs of track tabs or walls 38 define the gaps 34 therebetween. Pairs of flaps 40, extend from the pairs of track tabs 38 such that when the two removable tracks 30 are seated in the two grooves 20 the pairs of flaps 40 contact the top surface 22 of the couch 14 substantially sealing off the two grooves 20 from outside contaminates. Moreover, the flaps 40 are preferably formed at a depressed angle θ so that the flaps 40 are not horizontal and do not merely contact the top surface 22 of the couch 14. Rather, the depressed angle θ is less than 90 degrees, in a preferred embodiment it is 78 degrees, so that when the tracks 30 are seated or secured in the grooves 20 the flaps 40 are bent out and resilient forces urge them back toward the top surface 22 of the couch 14 creating a tight seal therewith.

Additionally, the flaps 40 are optionally tapered so that ends thereof sit more flush with the top surface 22 of the couch 14. In this manner, patient comfort is increased and the risk is reduced of the patient being gouged or scratch by a corner of the flaps 40 as he is placed on and/or removed from the couch 14.

The removable tracks 30 seal the grooves 20 from outside contaminates while, at the same time, being easily installed and removed, the tracks 30 themselves are readily cleaned, sanitized, replaced, or otherwise maintained. Additionally, the removable tracks 30 serve as a versatile universal connection or engagement point for patient support and restraint accessories. The removable tracks 30 provide a continuous longitudinal range over which one or more of the accessories may be adjustably positioned.

Figure 3A:
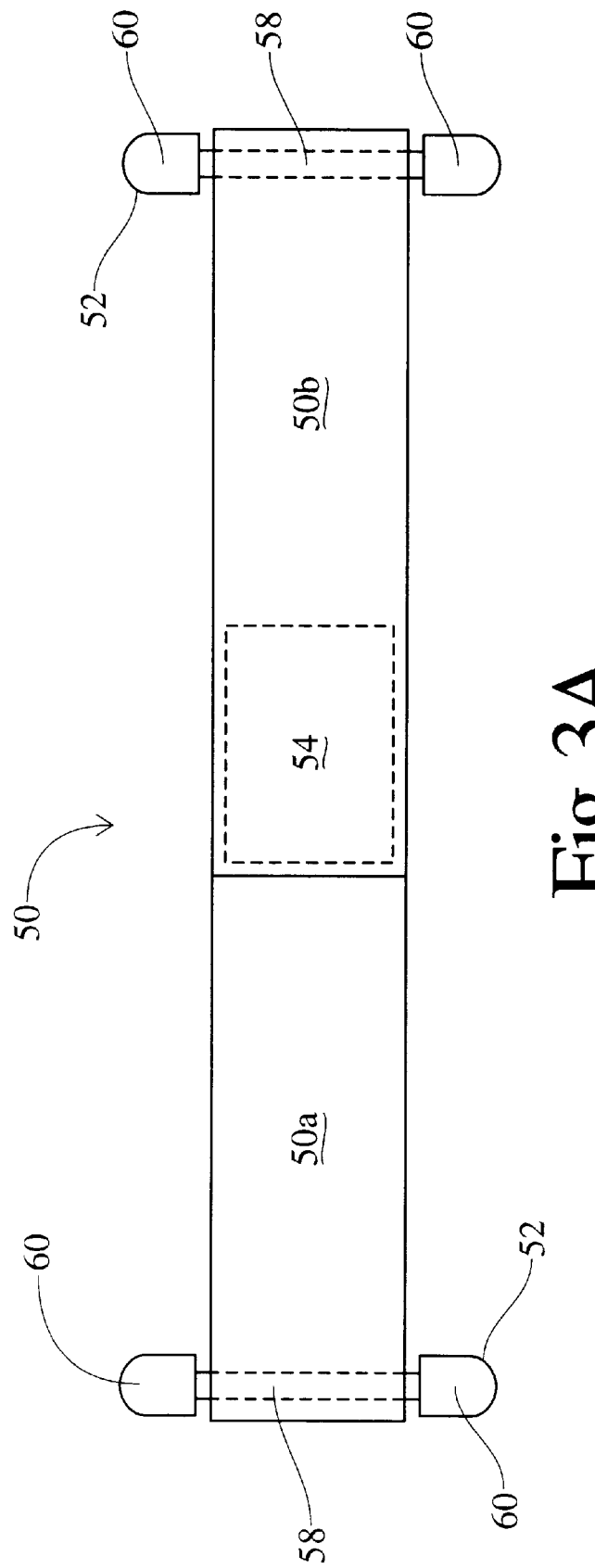
FIG. 3A is a top view of an adjustable patient restraint strap in accordance with aspects of the present invention.

More specifically, with reference to FIGS. 3A through 3C, a length adjustable patient restraint strap 50 has opposing ends attached to pins 52. The pins selectively engage the two removable tracks 30 thereby selectively securing opposing ends of the adjustable restraint strap 50 to opposite sides of the top surface 22 of the couch 14. That is to say, the pins 52 are sized to fit inside the hollow cylindrically shaped portions 32 of the tracks 30 without passing through the gaps 34. However, the pins 52 may pass through the gaps 34 at the insertion regions 36 thereof. In operation, one or more straps 50 having variable widths as desired are use to secure and/or immobilize the patient on the couch 14. The opposing pins 52 attached to opposite ends of the strap 50 are inserted through the top, via insertion regions 36, of opposing tracks 30 which are seated in the grooves 20. Optionally, the pins 52 are inserted from an end of the tracks 30. In either case, the gaps 34 are sized to permit the straps 50 passage therethrough while prohibiting the pins 52 passage therethrough. The pins 52 are then adjustably positioned as desired along a continuous longitudinal range of the tracks 30. The strap 50 is then adjust to the desired length and/or tightness. As the pins 52 and gaps 34 are appropriately sized so that the pins 52 do not pass through the gaps 34, when the straps 50 are tightened the patient is secured to the couch 14.

In a preferred embodiment, the strap 50 includes two parts 50a and 50b made from a polyester webbing or other suitable material. Each part has a securing end where the pin 52 is attached and an opposing joining end where a fastener 54 is attached that selectively joins the two parts 50a and 50b together at the desired length. The fastener 54 is the fastening tape type having a field of minute hooks that fasten to a corresponding field of uncut pile (i.e. Velcro). Optionally, other appropriate fasteners may be employed such as buckles, hooks, ties, buttons, D loops, or the like. The strap parts 50a, 50b are attached to the pins 52 by looping a length 56 thereof around a rod portion 58 of the pin 52 and stitching or otherwise joining it back to itself. Enlarged heads 60 of the pins 52 keep the straps 50 from sliding off the rod portions 58. Moreover, the enlarged heads 60 are sized to fit in the cylindrically shaped portion 32 of the tracks 30 with passing through the gaps 34.

With reference to FIGS. 4A and 4B and FIGS. 5A and 5B, a side board assembly including an engagement member 70 and a support member 72 is also selectively engaged with the removable tracks 30. The side board assembly is employed to support a part of the patient's anatomy off to the side of the couch 14. For example, an arm having an IV may be positioned thereon. Optionally, the side board may be used to hold a physician's medical instruments, surgical tools, or the like.

Figure 4A:
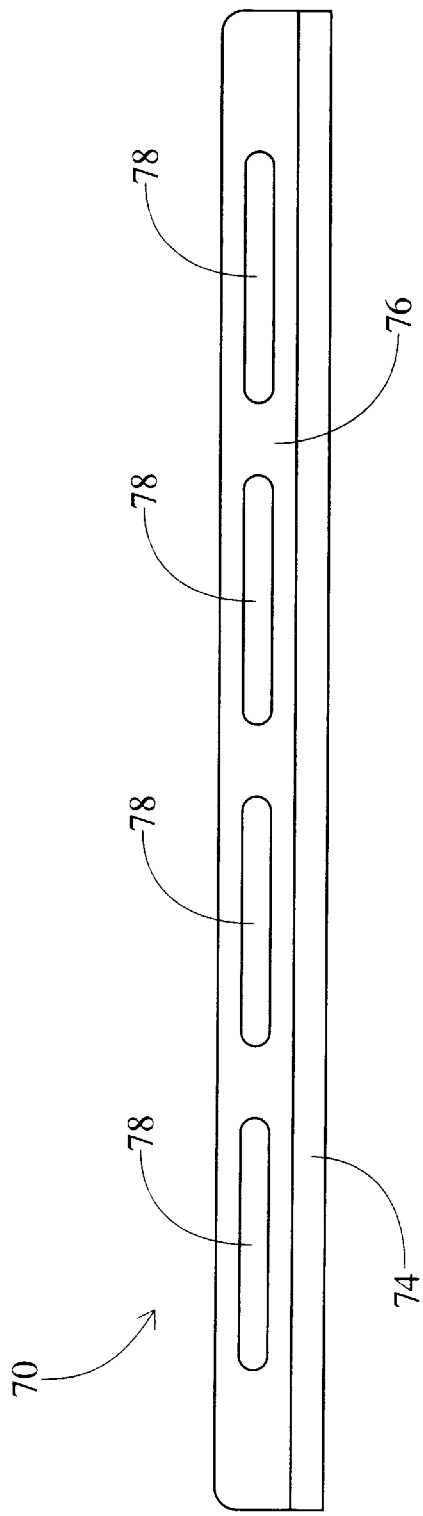
FIGS. 4A and 4B are side and end views respectively of an engagement member for a side board in accordance with aspects of the present invention.
Figure 4B:
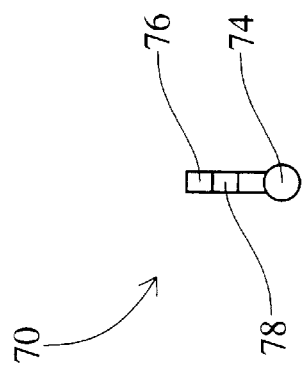

With particular reference to FIGS. 4A and 4B, the engagement member 70 selectively engages one of the removable tracks 30 thereby selectively securing it to the top surface 22 of the couch 14. The engagement member 70 includes a longitudinally extending cylindrical shaft 74 for selective engagement with one of the two removable tracks 30, and a shaft tab 76 radially extending from the shaft 74 that has a plurality of slots 78 formed therein. The shaft 74 is sized to fit in the cylindrically shaped portions 32 of the removable tracks 30 without passing through the gaps 34. When engaged with one of the two removable tracks 30 the shaft 74 is selectively positioned within the hollow cylindrically shaped portions 32 along a continuous longitudinal range of one of the two removable tracks 30 such that the shaft tab 76 passes through the gap 34 exposing the slots 78.

Figure 5A:
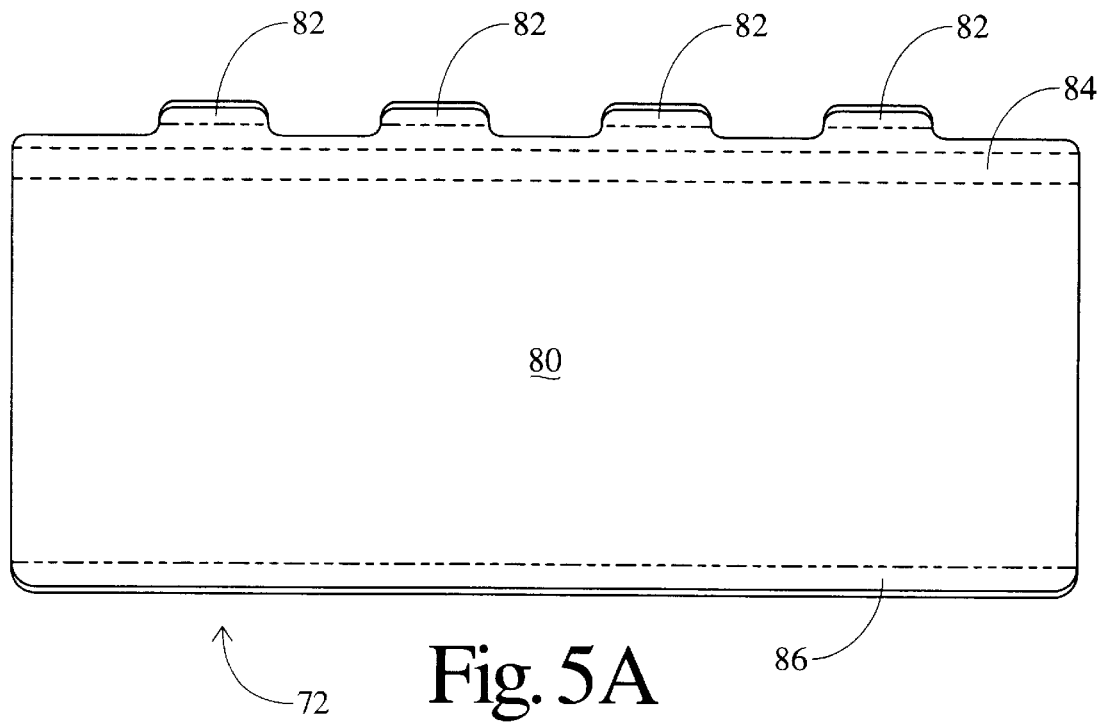
FIGS. 5A and 5B are top and end views respectively of a support member for the side board in accordance with aspects of the present invention; and, FIGS. 6A and 6B are side and end views respectively of an IV hook in accordance with aspects of the present invention.
Figure 5B:
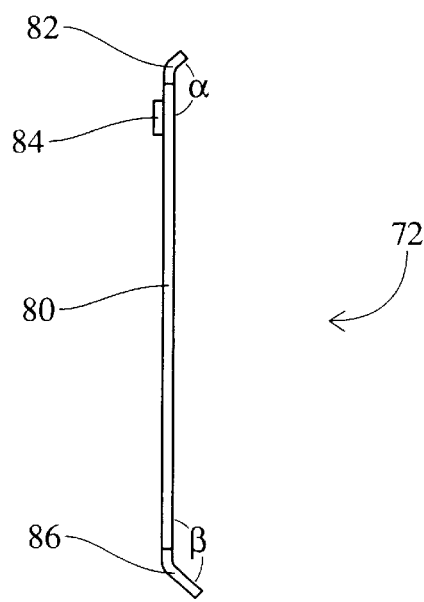

With particular reference to FIGS. 5A and 5B, the support member 72 has a surface 80 with a plurality of support member tabs 82 along one side thereof. The plurality of support member tabs 82 are selectively engaged with the plurality of slots 78 of the engagement member 70 by inserting the support member tabs 82 into the slots 78 thereby selectively securing the support member 72 to the engagement member 70. The plurality of support member tabs 82 are inclined at a predetermine angle α, preferably about 135 degrees, with respect to the surface 80 of the support member 72. When engaged, the natural weight of the support member along with the weight of objects thereon cooperate with the inclination of the plurality of support member tabs 82 to prohibit the support member 72 from sliding horizontally out and disengaging the support member tabs 82 from the slots 78. That is to say, in order for the support member 72 to be disengaged from the engagement member 70, the side of the support member 72 opposite the side including the support member tabs 82 is raised so that the inclined support member tabs 82 are horizontal and can therefore be drawn from the slots 78. The support member 72 also includes a bar 84 attached to an underside of the surface 80 of the support member 72 such that when the support member 72 is engaged with the engagement member 70 the bar 84 abuts up against the shaft tab 76 thereby supporting the surface 80 of the support member 72 in a substantially horizontal plane. A lip 86 along a side of the support member 72 opposite the plurality of support member tabs 82 is inclined at a predetermined angle β, preferably also 135 degrees, with respect to the surface 80 of the support member 72. The lip 86 helps to contain objects on the surface 80 of the side board which might otherwise potentially fall off.

Figure 6B:
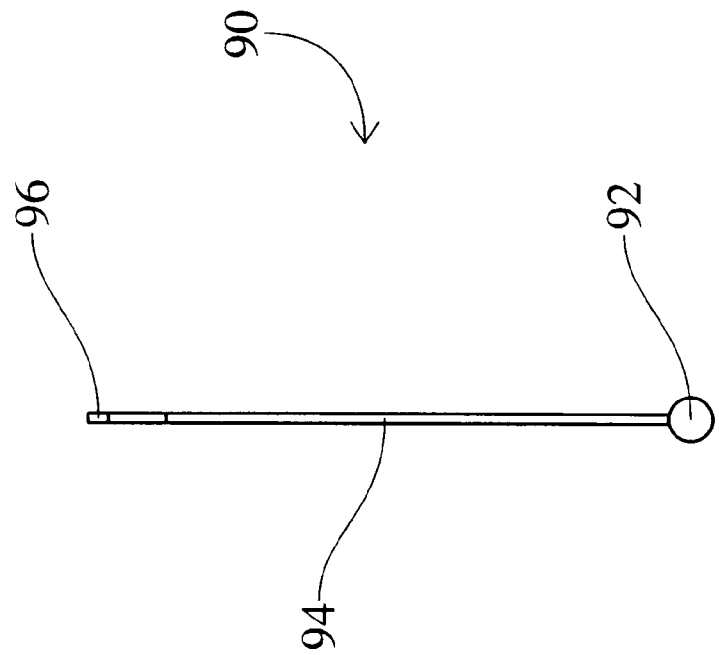
Figure 6A:
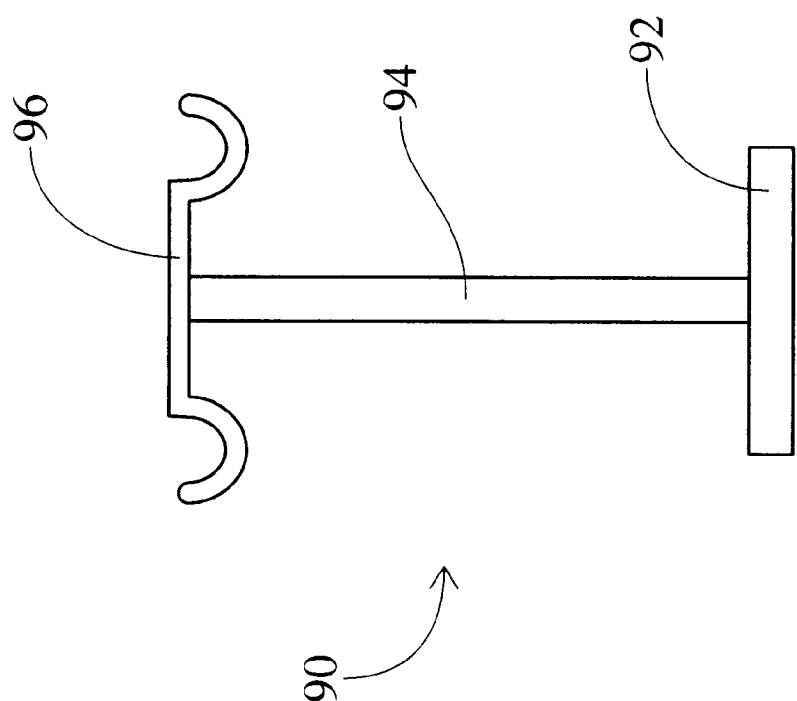

With reference to FIGS. 6A and 6B, an IV hook 90 for hanging IV bags and the like elevated above the patient is also selectively engaged with the removable tracks 30. The IV hook has an enlarged engagement portion 92 which is selectively engaged with one of the two removable tracks 30 thereby selectively securing the IV hook 90 to the couch 14. The enlarged engagement portion 92 has dimensions sized to fit the hollow cylindrically shaped portions 32 of the removable tracks 30 without passing through the gaps 34. When engaged in one of the tracks 30, the engagement portion 92 is selectively positioned within the hollow cylindrically shaped portion 32 along a continuous longitudinal range of the removable track 30 and an upwardly extending portion 94 rises from the engagement portion 92 through the gap 34. A hooked portion 96 from which the IV bags or other desired objects are hung is attached to an end of the upwardly extending portion 94 opposite the engagement portion 92.

While detailed above with reference to the hollow portions 32 of the tracks 30 being cylindrically shaped, any other appropriate shape (i.e. hollow rectangular or square tubes) is optionally employed so long as the parts sized to fit within the hollow portions 32 are prohibited from passing through the gaps 34, and they are adjustably positionable as desired along a continuous longitudinal range of the tracks 30.

The invention has been described with reference to the preferred embodiments. Obviously, modifications and alterations will occur to others upon a reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A versatile patient support and restraint system comprising:
   a couch having a top surface for supporting a patient being examined within an examination region;
   two substantially parallel grooves formed along a longitudinal direction in the top surface of the couch on opposite sides thereof;
   two removable tracks extending in a longitudinal direction, the removable tracks removably seated in the grooves; and,
   adjustable restraint straps for securing the patient to the couch, the adjustable restrain straps including;
      pins attached to opposing ends of the adjustable restraint straps which pins selectively engage the two removable tracks thereby selectively securing opposing ends of the adjustable restraint straps to opposite sides of the top surface of the couch.

2. The versatile patient support and restraint system according to claim 1, wherein the two removable tracks further include:
   hollow longitudinally extending cylindrically shaped portions with external diameters sized to fit in the two grooves and internal diameters sized to receive the pins of the adjustable restraint straps; and,
   longitudinally extending gaps formed in the cylindrically shaped portions creating openings along tops thereof, wherein the gaps are sized to permit the adjustable restraint straps to pass therethrough while prohibiting the pins from passing therethrough.

3. The versatile patient support and restraint system according to claim 2, wherein the gaps further include along lengths thereof insertion regions having lengths substantially equal to lengths of the pins wherein at the insertion regions the gaps are enlarged to permit the pins to pass therethrough.

4. The versatile patient support and restraint system according to claim 3, wherein the two removable tracks further include:
   pairs of track tabs running longitudinally along and extending radially from the cylindrically shaped portions which pairs of track tabs define the gaps therebetween; and,
   pairs of tapered flaps extending from the pairs of track tabs such that when the two removable tracks are seated in the two grooves the pairs of tapered flaps are urged toward the top surface of the couch substantially sealing off the two grooves from outside contaminates.

5. The versatile patient support and restraint system according to claim 2, wherein the pins are selectively positioned within the cylindrically shaped portions of the removable tracks along continuous longitudinal ranges thereof.

6. The versatile patient support and restraint system according to claim 2, wherein the adjustable restrain straps are adjustable in length and include two parts, wherein the two parts have securing ends where the pins are attached and opposing joining ends where a fastener is attached that selectively joins the two parts together.

7. The versatile patient support and restraint system according to claim 2, further comprising:

a side board, the side board including;
  an engagement member having a plurality of slots which engagement member selectively engages one of the two removable tracks thereby selectively securing it to the top surface of the couch; and,
  a support member having a surface with a plurality of support member tabs along one side thereof which plurality of support member tabs selectively engage with the plurality of slots of the engagement member to selectively secure the support member to the engagement member.

8. The versatile patient support and restraint system according to claim 7, wherein the engagement member includes:
  a longitudinally extending cylindrical shaft for selective engagement with one of the two removable tracks; and,
  a shaft tab radially extending from the shaft that has the plurality of slots formed therein.

9. The versatile patient support and restraint system according to claim 8, wherein the shaft is sized to fit in the cylindrically shaped portions of the removable tracks without passing through the gaps.

10. The versatile patient support and restraint system according to claim 9, wherein when engaged with one of the two removable tracks the shaft is selectively positioned along a continuous longitudinal range of one of the two removable tracks such that the shaft tab passes through the gap.

11. The versatile patient support and restraint system according to claim 7, wherein the plurality of support member tabs are inclined at a predetermine angle with respect to the surface of the support member.

12. The versatile patient support and restraint system according to claim 11, wherein the support member further includes:
  a bar attach to an underside of the surface of the support member such that when the support member is engaged with the engagement member the bar abuts up against the shaft tab.

13. The versatile patient support and restraint system according to claim 12, wherein the support member further includes:
  a lip along a side of the support member opposite the plurality of support member tabs which lip is inclined at a predetermined angle with respect to the surface of the support member.

14. The versatile patient support and restraint system according to claim 1, further comprising:
  an IV hook for hanging IV bags elevated above the patient, the IV hook having;
    an engagement portion which is selectively engaged with one of the two removable tracks thereby selectively securing the IV hook to the couch;
    an upwardly extending portion rising from the engagement portion; and,
    a hooked portion at an end of the upwardly extending portion opposite the engagement portion.

15. A patient restrain system in a diagnostic imaging apparatus having an imaging device which generates human viewable images of a patient's anatomy, an examination region where the patient is positioned for imaging, and a couch for supporting the patient in the examination region, the patient restrain system comprising:
  longitudinal grooves formed in a top surface of the couch;
  removable inserts secured in the longitudinal grooves which removable inserts substantially seal off the longitudinal grooves from outside contaminates; and,
  straps for securing the patient to the couch, wherein the straps have enlarged ends that are selectively engaged with the removable inserts thereby selectively securing the straps to the couch.

16. The patient restrain system of claim 15, wherein the removable inserts further include:
  longitudinally extending hollow portions with external dimensions sized to fit in the grooves and internal dimensions sized to receive the enlarged ends of the straps;
  longitudinally extending gaps formed in the hollow portions creating openings along tops thereof, wherein the gaps are sized to permit the straps to pass therethrough while prohibiting the enlarged ends from passing therethrough;
  pairs of walls running longitudinally along and extending from the hollow portions which pairs of walls define the gaps therebetween; and,
  pairs of flaps extending from the pairs of walls such that when the removable inserts are secured in the grooves the pairs of flaps are urged toward the top surface of the couch.

17. The patient restrain system of claim 16, wherein the enlarged ends are selectively positioned within the hollow portions of the removable inserts along continuous longitudinal ranges thereof.

18. The patient restrain system of claim 16, further comprising:
  a side board, the side board including;
    an engagement member having a plurality of slots which engagement member selectively engages the removable inserts thereby selectively securing it to the couch; and,
    a support member having a surface with a plurality of tabs along one side thereof which plurality of tabs selectively engage with the plurality of slots to selectively secure the support member to the engagement member.

19. The patient restrain system of claim 18, wherein the engagement member includes:
  an enlarged shaft for selective engagement with the removable inserts, the enlarged shaft having dimensions sized to fit the hollow portions of the removable inserts without passing through the gaps; and,
  an extending portion having the plurality of slots formed therein, the extending portion extending from the enlarged shaft through the gaps of the removable inserts.

20. The patient restrain system of claim 16, further comprising:
  an IV hook for hanging IV bags elevated above the patient, the IV hook having;
    an enlarged engagement portion which is selectively engaged with the removable inserts thereby selectively securing the IV hook to the couch, the enlarged engagement portion having dimensions sized to fit the hollow portions of the removable inserts without passing through the gaps;
    an upwardly extending portion rising from the enlarged engagement portion through the gaps; and,
    a hooked portion at an end of the upwardly extending portion opposite the enlarged engagement portion.

* * * * *